US010080886B2

(12) United States Patent
Crone et al.

(10) Patent No.: US 10,080,886 B2
(45) Date of Patent: *Sep. 25, 2018

(54) WEARABLE CARDIAC DEFIBRILLATION SYSTEM WITH FLEXIBLE ELECTRODES

(71) Applicant: West Affum Holdings Corp., Grand Cayman (KY)

(72) Inventors: William Edward Crone, Fall City, WA (US); Dallas Eugene Meeker, Kirkland, WA (US); Robert Reuben Buchanan, Bothell, WA (US); Douglas Keith Medema, Everett, WA (US); David Peter Finch, Bothell, WA (US); Laura Marie Gustavson, Redmond, WA (US); Daniel James Finney, Woodinville, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 15/800,027

(22) Filed: Oct. 31, 2017

(65) Prior Publication Data

US 2018/0064924 A1    Mar. 8, 2018

Related U.S. Application Data

(63) Continuation of application No. 14/710,799, filed on May 13, 2015, now Pat. No. 9,833,607.

(Continued)

(51) Int. Cl.
*A61N 1/00* (2006.01)
*A61N 1/04* (2006.01)
*A61N 1/39* (2006.01)

(52) U.S. Cl.
CPC .......... *A61N 1/0484* (2013.01); *A61N 1/046* (2013.01); *A61N 1/0492* (2013.01); *A61N 1/3968* (2013.01)

(58) Field of Classification Search
CPC .............................. A61N 1/0484; A61N 1/046
(Continued)

(56) References Cited

U.S. PATENT DOCUMENTS 3,724,355 A    4/1973   Unger
4,583,524 A    4/1986   Hutchins
(Continued)

FOREIGN PATENT DOCUMENTS

KR    101383806 B1    4/2014
WO    1998039061 A2   9/1998
WO    2010/151875 A1  12/2010

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Nadia A Mahmood
(74) *Attorney, Agent, or Firm* — Kavounas Patent Law Office, PLLC

(57) ABSTRACT

In embodiments, a wearable cardiac defibrillation (WCD) system includes one or more flexible ECG electrodes. The WCD system may have a support structure that is dimensioned to be worn so as to press the electrodes towards the body of the patient. The electrodes may be made from appropriate material so as to flex in order to match a contour of the body of the patient. An advantage over the prior art is that the flexible electrode may make better electrical contact (Continued)

with the patient's skin, and therefore provide a better ECG signal for the WCD system to perform its diagnosis.

20 Claims, 6 Drawing Sheets

Related U.S. Application Data

(60) Provisional application No. 62/072,818, filed on Oct. 30, 2014.

(58) Field of Classification Search
USPC .................................................. 607/5, 42
See application file for complete search history.

(56) References Cited

U.S. PATENT DOCUMENTS

| | | | |
|---|---|---|---|
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,437,083 B1 | 8/2002 | Brack et al. |
| 6,529,875 B1 | 3/2003 | Nakajima |
| 6,546,285 B1 | 4/2003 | Owen et al. |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,644,925 B2 | 2/2014 | Volpe et al. |
| 8,897,860 B2 | 11/2014 | Volpe et al. |
| 8,965,500 B2 | 2/2015 | Macho et al. |
| 9,008,801 B2 | 4/2015 | Kaib et al. |
| 9,131,901 B2 | 9/2015 | Volpe et al. |
| 9,132,267 B2 | 9/2015 | Kaib |
| 9,408,548 B2 | 8/2016 | Volpe et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0302860 A1 | 11/2012 | Volpe et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0039595 A1 | 2/2014 | Kroll-Orywahl et al. |
| 2014/0070957 A1 | 3/2014 | Longinotti-Buitoni et al. |
| 2014/0249613 A1 | 9/2014 | Kaib |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2016/0004831 A1 | 1/2016 | Carlson et al. |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Machine Translation of Korean Patent Document KR 101383806 B1, as procured from web by service of KIPO.

European Search Report for EP Application 15191436.3 dated Mar. 14, 2016.

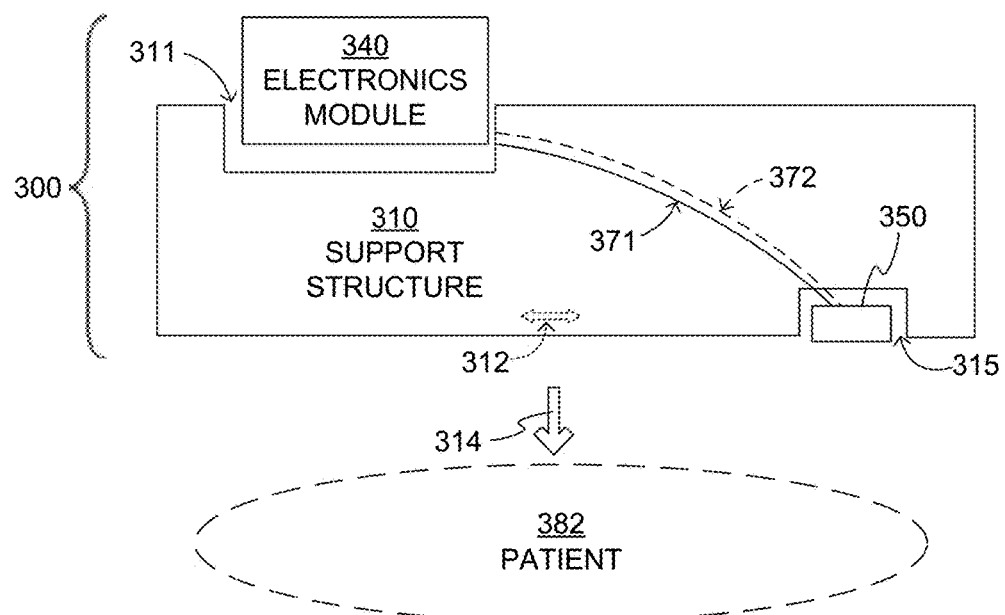
FIG. 3
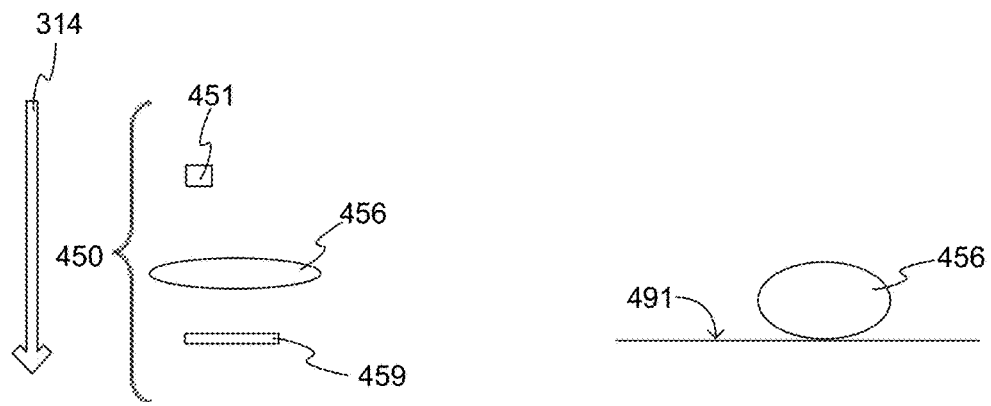
FIG. 4A  FIG. 4B

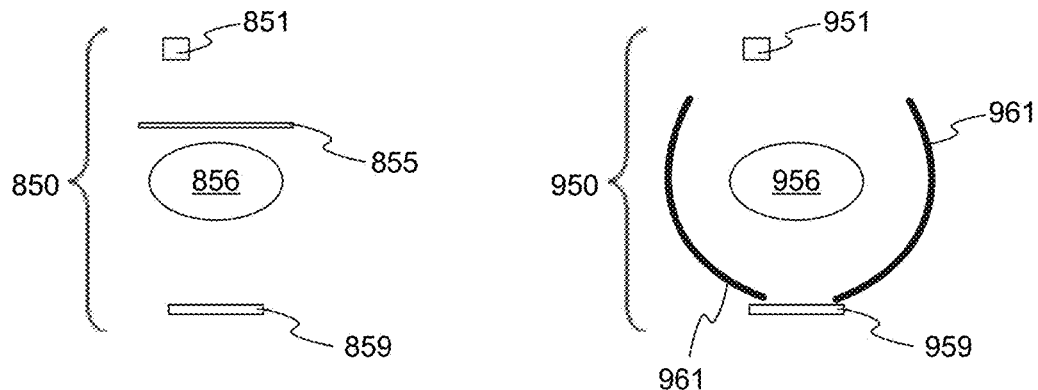
FIG. 8  FIG. 9
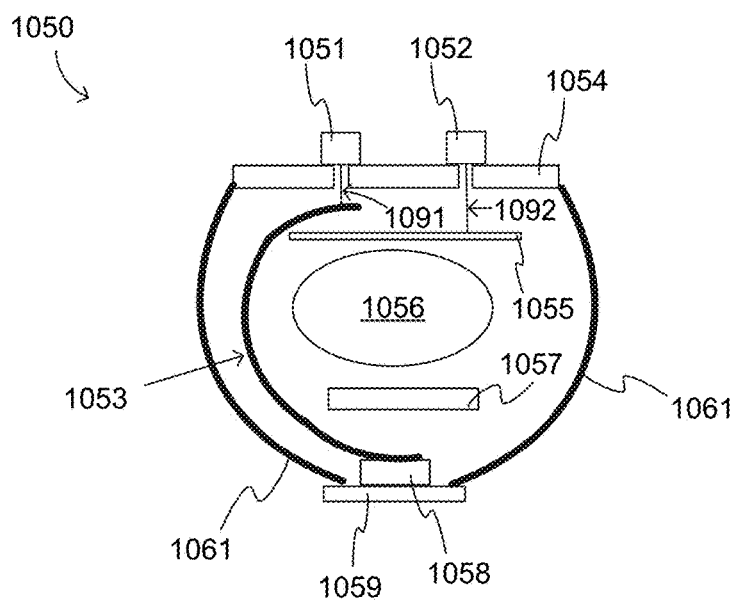
FIG. 10

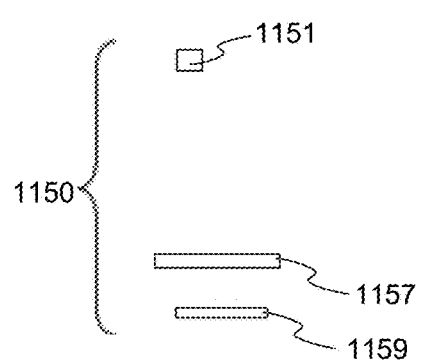
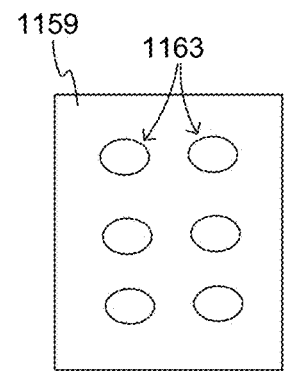
FIG. 11A          FIG. 11B
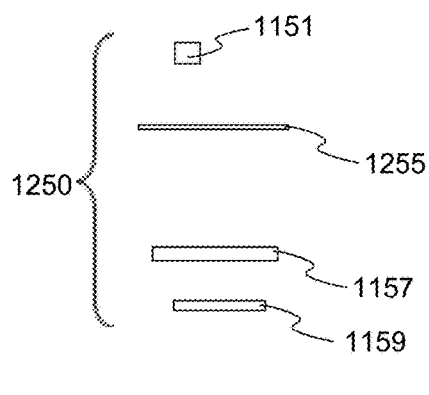
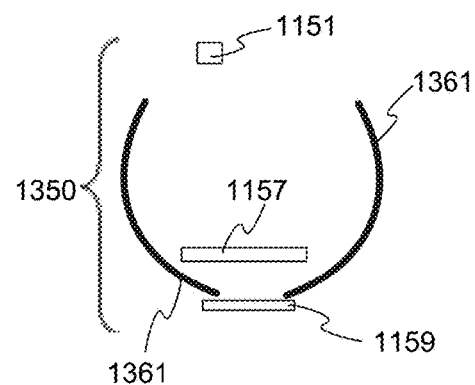
FIG. 12          FIG. 13

WEARABLE CARDIAC DEFIBRILLATION SYSTEM WITH FLEXIBLE ELECTRODES

CROSS REFERENCE TO RELATED PATENT APPLICATIONS

This patent application is a continuation of U.S. patent application Ser. No. 14/710,799 filed on May 13, 2015 and issued as U.S. Pat. No. 9,833,607 on Dec. 5, 2017, which in turn claims priority from U.S. Provisional Patent Application Ser. No. 62/072,818, filed on Oct. 30, 2014, the disclosure of which is hereby incorporated by reference.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a Wearable Cardiac Defibrillator ("WCD") system. A WCD system typically includes a harness, vest, or other garment that is configured to be worn by the patient. The WCD system includes a defibrillator and external electrodes, which are attached to the inside of the harness, vest, or other garment. When the patient wears the WCD system, the external electrodes can help monitor the patient's ECG. If a shockable heart arrhythmia is detected, then the defibrillator of the WCD system delivers the appropriate electric shock through the patient's body, and thus through the heart.

A challenge in the prior art remains with the monitoring electrodes. Electrodes may need to make good electrical contact with the patient's skin, without being intrusive or irritating the skin.

BRIEF SUMMARY

The present description gives instances of Wearable Cardiac Defibrillator (WCD) systems and electrode components for such systems, the use of which may help overcome problems and limitations of the prior art.

In embodiments, a wearable cardiac defibrillation (WCD) system includes one or more flexible ECG electrodes. The WCD system may have a support structure that is dimensioned to be worn so as to press the electrodes towards the body of the patient. The electrodes may be made from appropriate material so as to flex in order to match a contour of the body of the patient. An advantage over the prior art is that the flexible electrode may make better electrical contact with the patient's skin, and therefore provide a better ECG signal for the WCD system to perform its diagnosis.

In embodiments, a wearable cardiac defibrillation (WCD) system includes one or more electrode assemblies. The WCD system may have a support structure that is dimensioned to be worn so as to press the electrode assembly towards the body of the patient. The electrode assembly may have an electrode, and a signal terminal electrically coupled to the electrode. The electrode assembly may have a compressible pillow structure. The electrode assembly may have a moisture barrier so as to trap moisture from the patient's skin, for better conduction and lateral shifting of the electrode along the patient's skin. The electrode assembly may have an electrostatic shield between the electrode and the signal terminal so as to shield the electrode from electrical noise.

Embodiments may result in garments that integrate the disclosed electrode, and which can be washed with normal household methods. This allows for simple cleaning of lotions or patient's sweat from the electrodes, which may improve patient hygiene and reduce the chance of skin infections. All of this will add to the patient's overall comfort with the garment, and thus enhance their compliance with wearing the garment.

These and other features and advantages of this description will become more readily apparent from the Detailed Description, which proceeds with reference to the associated drawings in which:

BRIEF DESCRIPTION OF THE DRAWINGS

FIG. 3 is a diagram of sample components of a WCD system according to embodiments.

FIG. 4A is a diagram of some components of an electrode assembly of FIG. 1 that includes a pillow structure made according to embodiments and is applied to a patient's body under pressure.

FIG. 4B is a diagram of a detail of the pillow structure of the electrode assembly of FIG. 4A, as it is deposited on a flat surface.

FIG. 8 is a diagram of sample components of an electrode assembly, which is made according to embodiments that include an electrostatic shield.

FIG. 9 is a diagram of sample components of an electrode assembly, which is made according to embodiments that include a cover.

FIG. 10 is a diagram of a sample electrode assembly according to an embodiment.

FIG. 11A is a diagram of sample components of an electrode assembly, which is made according to embodiments that include a moisture barrier.

FIG. 11B is a top view of a main surface of an electrode that may be used in the assembly of FIG. 11A according to an embodiment.

FIG. 12 is a diagram of sample components of an electrode assembly, which is made according to embodiments that include an electrostatic shield.

FIG. 13 is a diagram of sample components of an electrode assembly, which is made according to embodiments that include a cover.

DETAILED DESCRIPTION

As has been mentioned, the present description is about Wearable Cardiac Defibrillator (WCD) systems and electrode components for such systems. Embodiments are now described in more detail.

Figure 1:
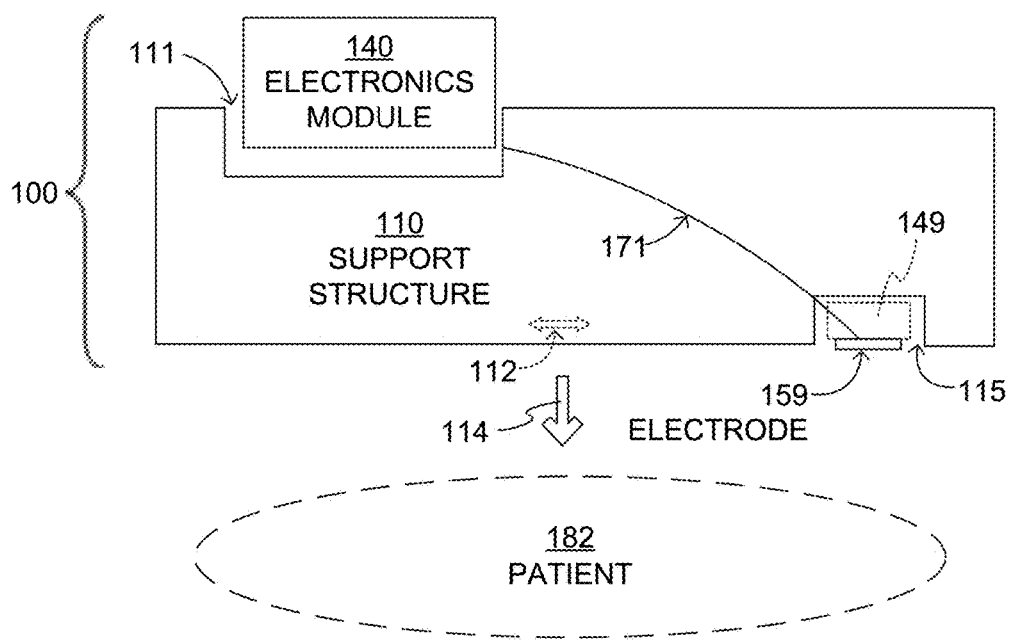
FIG. 1 is a diagram of sample components of a Wearable Cardiac Defibrillator (WCD) system according to embodiments.

FIG. 1 is a diagram of sample components 100 of a WCD system according to embodiments. Components 100 are intended to be worn by a patient 182, typically according to specific instructions. Only a section of the body of patient 182 is shown, which can be the torso, or other bodily part.

Components 100 of a WCD system are now described in more detail. Components 100 include a support structure 110, which is shown partly abstractly in FIG. 1. Support structure 110 can be configured to be worn by patient 182, typically according to a design. Support structure 110 can thus be part of a belt, a harness, a garment, a holster, and so on. In some embodiments, the wearable medical system includes a single support structure 110. In other embodiments, more support structures may be included.

Support structure 110 can be dimensioned relative to the body of patient 182 to be worn with internal tension 112. This dimensioning may be accomplished by, for example, making a portion be of adjustable length. In other words, in some embodiments at some times support structure 110 does not fit patient 182 everywhere loosely, but is worn with non-zero internal tension 112. Tension 112 is tension of non-zero magnitude that is internal to support structure 110, and which can cause pressure 114 to be exerted onto the body of patient 182 when support structure 110 is worn. Pressure 114 may squeeze the body of patient 182, preferably only gently. Internal tension 112, and its resulting pressure 114, may ensure that any electrodes of the WCD system make good electrical contact with the body of patient 182. Accordingly, support structure 110 can be a continuous band, or have clasps (not shown) that lock together, etc.

Components 100 also include an electronics module 140. Electronics module 140 can be a part of a wearable medical system that performs any one or more of the following functions: monitor physiological signals of patient 182, make determinations from these signals, communicate with the patient or with entities remote from the patient, store electrical energy for defibrillation, defibrillate, and so on.

Electronics module 140 can be configured to be coupled to support structure 110. Coupling can be permanent, such as attaching. In some embodiments, however, electronics module 140 can be coupled to and uncoupled from support structure 110, by the manufacturer, by patient 182, and so on. For example, electronics module 140 can be thus coupled by being inserted in a special pocket 111, and so on.

Components 100 additionally include an electrode 159, which can be an ECG electrode. Electrode 159 can be stand-alone, or it may be attached to an additional component 149 of an electrode assembly. Electrode assemblies are described in more detail later in this document, and may have even more components. While only one electrode 159 is shown, of course more may be used.

Whether part of an electrode assembly or not, electrode 159 can be configured to be coupled to support structure 110, so that electrode 159 remains pressed against the body of patient 182 due to nonzero pressure 114, when support structure 110 is worn by patient 182 as designed. As will be seen, a number of configurations of components 100 may accomplish this. For example, electrode 159 could be physically attached to support structure 110, for example by being constructed permanently into it, be received into a suitable pocket 115, etc. Moreover, electrode 159 could be coupled to support structure 110 but not be permanently physically attached to it. Electrode 159 can be coupled to the skin of patient 182 by contacting the skin directly, or indirectly over clothing, depending on whether the electrode is dry or not, etc. Even when physically coupled to the skin over clothing, some electrodes can achieve electrical coupling with the patient's skin through the clothing.

Electrode 159 is of course conductive. This is written explicitly in this document, because electrode 159 can be made according to embodiments from materials that are unusual for electrodes.

Figure 2A:
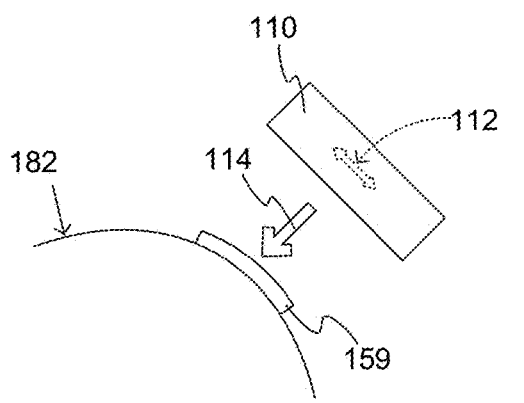
FIG. 2A is a diagram of a detail of a flexible electrode of FIG. 1 that is made according to embodiments, and is applied to a patient's body under pressure.

Electrode 159 may also be flexible. For example, it may bend under pressure 114. As can be seen in FIG. 2A, electrode 159 is flexible enough so as to acquire a first shape due being subjected to nonzero pressure 114 when support structure 110 is worn by patient 182. The first shape of FIG. 2A is bent, as flexible electrode 159 follows a curved contour of the body of patient 182. In FIG. 2A, support structure 110 is shown even more abstractly than in FIG. 1. Due to the flexibility, electrodes according to embodiments can be integrated into a support structure in such a way as to have fairly even pressure across the complete electrode thereby reducing any perceived "pressure points" by the patient, and thus be more comfortable and increase patient compliance.

Figure 2B:
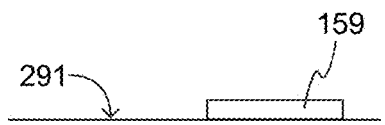
FIG. 2B is a diagram of a detail of the electrode of FIG. 2A, as it is deposited on a flat level surface.

In addition, as can be seen in FIG. 2B, electrode 159 is flexible enough so as to acquire a second shape, if electrode 159 alone is deposited on a flat level surface 291 without being subjected to an external pressure. The second shape is flat, which is different from the first shape of FIG. 2A. Of course, to replicate the exact situation of FIG. 2B electrode 159 may have to be separated from any electrode assembly. The ability to acquire the second shape so as to demonstrate the flexibility can sometimes be confirmed even without such a separation.

The flexibility of electrode 159 can be such that it transitions from the first shape to the second shape and vice versa immediately, or after some time. This time is preferably less than 1 hour, and preferably less than 10 min. Accordingly, hard materials like large pieces of metal may not serve well.

The views of FIGS. 1, 2A, 2B are side views of electrode 159. Electrode 159 may have a main surface, for example as shown in electrode 1159 in FIG. 11B. The main surface of electrode 1159 is shown as rectangular, but it can be circular, oval, or of other shapes. The main surface may have a surface area of, say, 1 $cm^2$ to several $cm^2$.

In some embodiments, electrode 159 may be 2 cm on the side. The amount of curvature shown in FIG. 2A may be larger than is the case for typical locations of the body of patient 182, but the exaggeration in curvature is used in FIG. 2A to demonstrate the flexibility of electrode 159.

The views of electrode 159 in FIGS. 1, 2A, 2B show its thickness, because they are side views. This thickness can be the height of protruding above the level of surface 291 in FIG. 2B. In embodiments, electrode 159 is further thin, which means it has a small thickness. The thickness, then, can be measured in a direction perpendicular to the main surface. For example, electrode 159 may have an average thickness of less than 4 mm, less than 2 mm, or even less than 1 mm, for example 0.5 mm.

Electrode 159 may be made in a number of ways. For example, it can include a metal foil, such as aluminum or copper foil. Such a foil could be attached to a side of a piece of foam. Alternately, electrode 159 can include a material that includes polyurethane, or conductive polyurethane that contains one of carbon, carbon nanotubes, particles of a metal, and metal nanoparticles. Alternately, electrode 159 can include silicone, a conductive silicone rubber, and so on. The conductive silicone rubber may be enriched with conductive elements such as carbon, carbon nanotubes, particles of a metal, metal nanoparticles, and so on. Electrode 159 may also include a material that includes polydimethylsiloxane (PDMS) silicone rubber, perhaps enriched with conductive elements such as mentioned above. Electrodes formed from silicone rubber with added conductive fillers can be more resistive than capacitive in nature. This resistive component allows for various features to be added that cannot be implemented with capacitive electrodes. First, the amplifier can generate a dc coupled driven lead which is used to reduce common mode on the patient. This is often referred to as a Right Leg Drive though the electrode can be placed in various places. Some capacitive electrodes cannot be used for driven leads at frequencies that compensate for patient movement and power line interference. Using electrodes made from a silicone rubber greatly increases signal quality using driven leads. The resistive component also allows the use of a "dc leads off" method for detecting when an electrode is not in good contact with the patient. This is both a simpler and more robust leads off method than the "ac leads off" required by capacitive electrodes. Embodiments of a silicone electrode can thus be made without any electronics supporting the electrode itself. In addition, electrodes thus formed from silicone rubber might not be affected much by commonly available lotions, and so the patient is free to use these both for general use or to minimize any effects of using the electrodes if the patient has very sensitive skin.

In choosing a material, care should be taken so that the material contacting the patient is biocompatible with the skin of the patient. Accordingly, if electrode 159 is worn over a garment, the material may not matter very much. If, however, electrode 159 is configured to contact the skin directly so it can make ohmic contact with it, then a material like aluminum may not be preferred. Ohmic contact makes for excellent signal quality. The electrode could be made capacitive, if need be.

Returning to FIG. 1, components 100 may include a signal conductor 171. Signal conductor 171 can be configured to couple electronically electronics module 140 and electrode 159 when electronics module 140 is coupled to support structure 110 and support structure 110 is worn by patient 182 as per the instructions for use. Signal conductor 171 may include a wire, a cable and so on. It may be integrated with support structure 110 at least in part, for example retained by special loops of it, suitable pockets of it, etc. Standard ECG cabling techniques can be used even with the silicone electrodes, because they generate a signal similar to that generated by a standard adhesive electrode.

FIG. 3 is a diagram of sample components 300 of a WCD system according to embodiments. Components 300 include an electronics module 340 that can be made as electronics module 140, and a support structure 310 that can be made as described for support structure 110, adapted for differences. Support structure 310 may include a suitable pocket 311 for electronics module 340, and can be configured to be worn by a patient 382. Support structure 310 can be dimensioned relative to a body of patient 382 to be so worn with nonzero internal tension 312, which causes nonzero pressure 314 to be exerted onto the body.

Components 300 additionally include an electrode assembly 350. Electrode assembly 350 can be configured to be coupled to support structure 310 so that electrode assembly 350 remains pressed against the body of patient 382 due to nonzero pressure 314, when support structure 310 is worn by patient 382. A number of configurations of components 300 may accomplish this. For example, electrode assembly 350 could be physically attached to support structure 310, for example by being constructed permanently into it, be received into a suitable pocket 315, etc. Moreover, electrode assembly 350 could be coupled to support structure 310 but not be permanently physically attached to it.

Electrode assembly 350 can be constructed in many different ways. It can have components selected from many possible components. Examples are now described.

Referring to FIG. 4A, some components 450 are shown according to embodiments, which can be the components of electrode assembly 350. Components 450 include an electrode 459, which can be an ECG electrode. Electrode 459 can be made in any way known in the art, including ways described earlier in this document for flexible electrode 159.

Components 450 additionally include a signal terminal 451. In embodiments where electrode assembly 350 is removable from support structure 310, signal terminal 451 can advantageously be part of an electro-mechanical connector. An electro-mechanical connector can be implemented in many ways according to embodiments as is known in the art, for example with connector components that make a mechanical connection, and also complete an electrical connection upon making a mechanical connection. These electro-mechanical connectors include elements such as hooks, buttons, etc. Another example of an electro-mechanical connector is a snap mechanical contact, which is also known as a snap fastener. This snap mechanical contact may match matingly with another snap mechanical contact of support structure 310 for coupling and uncoupling. For example, one can be male and the other can be female.

Signal terminal 451 can be electrically coupled to electrode 459, which is a feature not shown in FIG. 4A but is described later in this document. This coupling should be made with a view to accommodating what is physically between signal terminal 451 and electrode 459 in each embodiment.

Returning to FIG. 3, components 300 may include a signal conductor 371. Signal conductor 371 can be configured to couple electronically electronics module 340 and signal terminal 451 when electronics module 340 is coupled to support structure 310 and support structure 310 is worn by patient 382. Signal conductor 371 may include a wire, a cable and so on, and may be integrated with support structure 310 as described for signal conductor 171. Signal conductor 371 may have a first end and a second end, to accomplish the coupling. For example, the first end of signal conductor 371 may terminate in a first electro-mechanical connector that is on support structure 310, and the signal terminal of an electrode assembly that is electrically coupled to the electrode can be part of a second electro-mechanical connector that can match matingly the first electro-mechanical connector. The first electro-mechanical connector and the second electro-mechanical connector can be made as mentioned above, for example they can include snap mechanical contacts, etc.

Returning to FIG. 4A, components 450 additionally include a pillow structure 456. Pillow structure 456 can be between electrode 459 and signal terminal 451.

Pillow structure 456 can be flexible, and pressure 314 can maintain good electrical contact. The reduced pressure can thus help improve patient compliance with wearing the WCD system. So, pillow structure 456 can be flexible enough so as to acquire a first shape due to the electrode assembly being subjected to nonzero pressure 314 when support structure 310 is worn. As seen in FIG. 4A, this first shape is somewhat flattened. As seen in FIG. 4B, pillow structure 456 can be flexible enough so as to acquire a second shape if pillow structure 456 alone is deposited on a flat level surface 491 without pillow structure 456 being subjected to an external pressure such as pressure 314. The second shape is different from the first shape, it is less flattened. In this case, the first shape is a squeezed version of the second shape. Of course, to replicate the exact situation of FIG. 4B, pillow structure 456 may have to be separated from the remainder of the electrode assembly. The ability to acquire the second shape as to demonstrate the flexibility can sometimes be confirmed even without such a separation.

Pillow structure 456 may be made in a number of ways. For example, it can include a piece of an open-celled foam, or a pouch filled with a fluid, such as air, a liquid, etc. Foam works well when it is resilient enough, since it is a single material. In some embodiments, the pillow structure includes a pouch that has a spring.

As mentioned above, an electrode assembly according to embodiments may further include a flexible inner conductor. The signal terminal can be electrically coupled to the electrode via the flexible inner conductor. For example, the flexible inner conductor can be electrically coupled to the signal terminal, to the electrode, or to both. The flexible inner conductor may flex when pillow structure 456 transitions from the first shape, e.g. of FIG. 4A, to the second shape, e.g. to that of FIG. 4B. Examples are now described.

Figure 5:
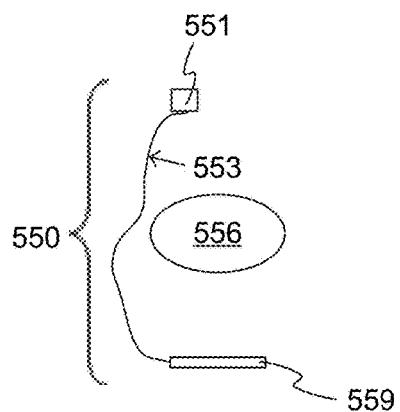
FIG. 5 is a diagram of sample components of an electrode assembly, which is made according to embodiments that include a flexible inner conductor.

Referring to FIG. 5, some components 550 are shown according to embodiments, which can be the components of electrode assembly 350. Components 550 include an electrode 559 that can be as described for electrode 459, a signal terminal 551 that can be as described for signal terminal 451, and a pillow structure 556 that can be as described for pillow structure 456.

Components 550 moreover include a flexible inner conductor 553, which is a wire. Flexible inner conductor 553 is electrically coupled to both signal terminal 551 and to electrode 559.

Figure 6A:
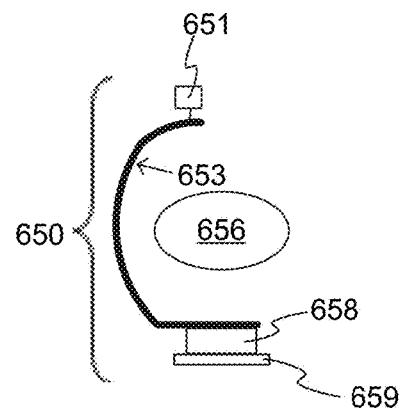
FIG. 6A is a diagram of sample components of an electrode assembly, which is made according to embodiments that include a flexible inner conductor which has a fabric that is coated with a metal.

Referring to FIG. 6A, some components 650 are shown according to embodiments, which can be the components of electrode assembly 350. Components 650 include an electrode 659 that can be as described for electrode 459, a signal terminal 651 that can be as described for signal terminal 451, and a pillow structure 656 that can be as described for pillow structure 456.

Components 650 moreover include a flexible inner conductor 653, which includes a fabric. The fabric can operate as a flexible substrate, and be advantageously coated with a metal, such as silver. Flexible inner conductor 653 is electrically coupled directly to signal terminal 651, and indirectly to electrode 659. In particular, flexible inner conductor 653 is coupled to electrode 659 via a conductive adhesive 658. Alternately, a conductive double-sided pressure sensitive adhesive tape could be used, etc. Or, electrode 659 could also be intrinsically molded through or around the flexible conductor. Or, flexible inner conductor 653 can include a conductive fabric that is overmolded with the electrode.

Figure 6B:
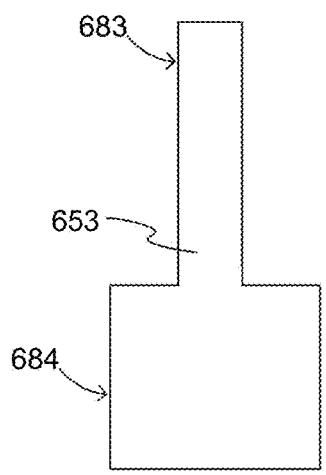
FIG. 6B is a top view of a flexible inner conductor of FIG. 6A according to an embodiment.

Flexible inner conductor 653 can be planar. FIG. 6A shows only a side view of it. Referring to FIG. 6B, a top view of conductor 653 is shown, where the fabric substrate is laid flat on a surface and the metal coating is not differentiated. In this example, conductor 653 has a large portion 684 that is substantially coextensive with the main surface of electrode 659, and a small portion 683 that is large enough to make contact with signal terminal 651.

Figure 7:
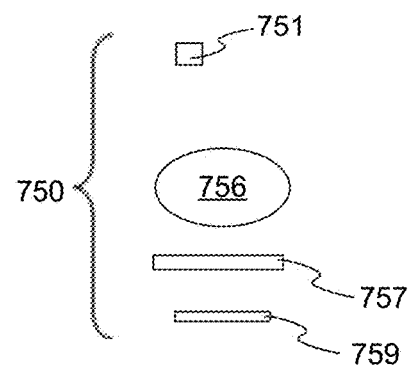
FIG. 7 is a diagram of sample components of an electrode assembly, which is made according to embodiments that include a moisture barrier.

Referring to FIG. 7, some components 750 are shown according to embodiments, which can be the components of electrode assembly 350. Components 750 include an electrode 759 that can be as described for electrode 459, a signal terminal 751 that can be as described for signal terminal 451, and a pillow structure 756 that can be as described for pillow structure 456.

Components 750 moreover include a moisture barrier 757. Moisture barrier 757 is between electrode 759 and signal terminal 751. In this case where pillow structure 756 is provided, moisture barrier 757 is between electrode 759 and pillow structure 756.

In some embodiments, electrode 759 has a main surface that has holes. This feature is not shown in FIG. 7, but is shown in FIG. 11B.

Moisture barrier 757 of FIG. 7 is intended to not permit water vapor to escape from the patient's skin. The trapped water vapor improves conductivity of the electrode, and the quality of the detected signal.

Accordingly, moisture barrier 757 is made from a material that is substantially impermeable to water vapor so as to slow down the evaporation from the skin. This means that, if moisture barrier 757 is made from a material that has pores, these pores are not large enough to permit the skin to dry out in the usual conditions that the patient is expected to wear the WCD system. Candidates are any continuous-surface material, even metal foil or a continuously coated water-resistant fabric material, such as the material that is sometimes used to make raincoats. Other materials can be a thin polymer membrane, such as a urethane or silicone based material.

Referring to FIG. 8, some components 850 are shown according to embodiments, which can be the components of electrode assembly 350. Components 850 include an electrode 859 that can be as described for electrode 459, a signal terminal 851 that can be as described for signal terminal 451, and a pillow structure 856 that can be as described for pillow structure 456.

Components 850 moreover include an electrostatic shield 855. Electrostatic shield 855 is between signal terminal 851 and electrode 859. In this particular embodiment, electrostatic shield 855 is between signal terminal 851 and pillow structure 856. Electrostatic shield 855 is intended to shield electrode 859 from any signals that may be traveling along any other signal conductors of the WCD system, and which are physically close to the electrode assembly. Electrostatic shield 855 may shield electrode 859 from varying electric fields that are external to the patient. Such could be formed by clothing that has a static charge moving relative to electrode 859 or from another person who has a static charge moving in close proximity to the patient. There are other sources of varying electric fields as well.

Electrostatic shield 855 can be made in a number of ways. In embodiments, it can be made from a metal foil, such as copper. Electrostatic shield 855 is preferably protected from contacting the flexible conductor, and insulating is one way to do this. Accordingly, electrostatic shield 855 is sometimes a foil covered by an insulating tape.

Referring to FIG. 9, some components 950 are shown according to embodiments, which can be the components of electrode assembly 350. Components 950 include an electrode 959 that can be as described for electrode 459, a signal terminal 951 that can be as described for signal terminal 451, and a pillow structure 956 that can be as described for pillow structure 456.

Components 950 moreover include a cover 961. Cover 961 may surround pillow structure 956 at least in part. In some embodiments cover 961 is flexible, and flexes when pillow structure 956 transitions from the first shape to the second shape. Cover 961 may be made from any suitable material, such as fabric, plastic, etc.

In some embodiments, cover 961 surrounds pillow structure 956 completely. In other embodiments, the electrode assembly further includes a backing which, together with cover 961, completely surround pillow structure 956. An example is now described.

Referring to FIG. 10 an electrode assembly 1050 is shown, which is made according to an embodiment. Electrode assembly 1050 is a standalone electrode assembly. Whether standalone or not, electrode assembly 1050 can be used for electrode assembly 350.

Electrode assembly 1050 includes an electrode 1059 that can be as described for electrode 459, a signal terminal 1051 that can be as described for signal terminal 451, and a flexible inner conductor 1053 that can be as described for flexible inner conductor 653. In this particular example, signal terminal 1051 can be part of a snap mechanical contact. Flexible inner conductor 1053 is electrically coupled directly to signal terminal 1051, and indirectly to electrode 1059 via a conductive adhesive 1058.

Electrode assembly 1050 also includes a pillow structure 1056 that can be as described for pillow structure 456, a moisture barrier 1057 that can be as described for moisture barrier 757, and an electrostatic shield 1055 that can be as described for electrostatic shield 855.

Electrode assembly 1050 additionally includes a reference terminal 1052. Reference terminal 1052 is coupled to electrostatic shield 1055, and can serve as electrical ground. In this embodiment, reference terminal 1052 can be part of a snap mechanical contact, similarly with signal terminal 1051. In such embodiments, the WCD system may also include a reference conductor 372, which can be seen in FIG. 3. Reference conductor 372 can be configured to couple electronically electronics module 340 and reference terminal 1052, when electronics module 340 is coupled to support structure 310 and support structure 310 is worn by patient 382.

Electrode assembly 1050 moreover includes a backing 1054, on which signal terminal 1051 and reference terminal 1052 are provided. Backing 1054 can be made from a hard plastic, or other suitable material. The snap mechanical contacts of signal terminal 1051 and reference terminal 1052 are on backing 1054. These snap mechanical contacts permit electrode assembly 1050 to be removable from the support structure. Signal terminal 1051 and reference terminal 1052 are electrically connected with wire stubs 1091, 1092 that go through suitable openings in backing 1054.

Electrode assembly 1050 further includes a cover 1061 that can be as described for cover 961. Backing 1054, together with cover 1061, completely surround pillow structure 1056.

In FIG. 10 the various components have been drawn with their appropriate relationships. To improve clarity, space has been added between the components that might not be there in actual embodiments. For example, wire stub 1091 can be shorter, and inner conductor 1053 may be touching backing 1054. Moreover, electrostatic shield 1055 might be attached to inner conductor 1053 and backing 1054, with wire stub 1092 being accordingly shorter. Pillow structure 1056 might be much larger, pushing moisture barrier onto inner conductor 1053 and against electrode 1059, while uniformly stretching cover 1061. In fact, while inside the cover, pillow structure 1056 might be somewhat compressed compared to, say, how pillow structure 456 is shown in FIG. 4B.

Referring to FIG. 11A, some components 1150 are shown according to embodiments, which can be the components of electrode assembly 350. Components 1150 include an electrode 1159 that can be as described for electrode 459, a signal terminal 1151 that can be as described for signal terminal 451, and a moisture barrier 1157 that can be as described for moisture barrier 757.

FIG. 11B is a top view of the main surface of electrode 1159. It will be observed that electrode 1159 has holes or pores 1163. If moisture barrier 1157 is indeed provided, it can cause moisture to be generated from the skin as described above, which holes 1163 can capture.

Unlike with FIG. 7, components 1150 do not include a pillow structure, although it could. However, components 1150 may include other features that were already described, for example an electrostatic shield 1255 as shown in FIG. 12 for electrode assembly components 1250, a cover 1361 as shown in FIG. 13 for electrode assembly components 1350, and so on.

Figure 14:
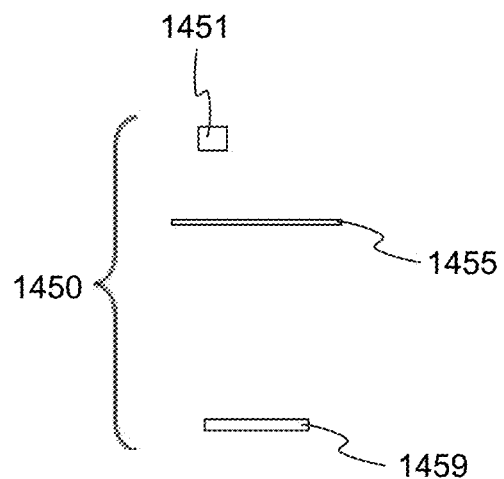
FIG. 14 is a diagram of sample components of an electrode assembly, made according to embodiments that include an electrostatic shield.

Referring to FIG. 14, some components 1450 are shown according to embodiments, which can be the components of electrode assembly 350. Components 1450 include electrode 1459 that can be as described for an electrode 459, a signal terminal 1451 that can be as described for signal terminal 451, and an electrostatic shield 1455 that can be as described for electrostatic shield 855.

Figure 15:
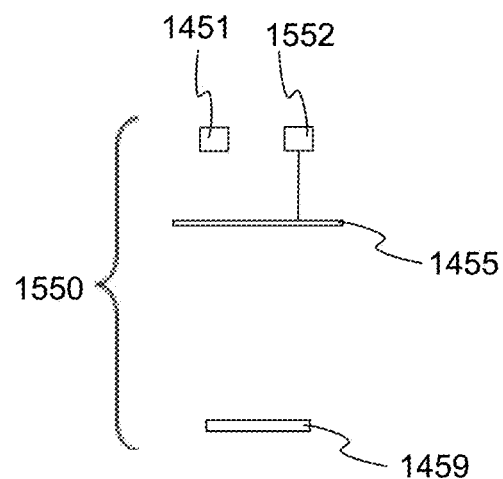
FIG. 15 is a diagram of sample components of an electrode assembly, made according to embodiments that include an electrostatic shield and a corresponding reference terminal.

Unlike with FIG. 8, components 1450 do not include a pillow structure. However, components 1150 may include other features that were already described, for example a reference terminal 1552 as shown in FIG. 15 for electrode assembly components 1550, and so on.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet (ADS) of this patent application, are hereby incorporated by reference herein, including any priority claims made in those applications and any material incorporated by reference, to the extent such subject matter is not inconsistent herewith.

In this description a single reference numeral may be used consistently to denote a single aspect, component, or process. Moreover, a further effort may have been made in the drafting of this description to choose similar though not identical reference numerals to denote versions or embodiments of an aspect, component or process that are the same or possibly different. Where made, such a further effort was not required, but was nevertheless made gratuitously to accelerate comprehension by the reader. Even where made in this document, such an effort might not have been made completely consistently throughout the many versions or embodiments that are made possible by this description. Accordingly, the description controls. Any similarity in reference numerals may be used to confirm a similarity in the text, or even possibly a similarity where express text is absent, but not to confuse aspects where the text or the context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A Wearable Cardiac Defibrillator (WCD) system, comprising:
    a support structure configured to be worn by a patient;
    an electronics module;
    an electrode assembly configured to be coupled to the support structure so that the electrode assembly is placed against the body when the support structure is so worn, the electrode assembly including an electrode, a signal terminal electrically coupled to the electrode, and a moisture barrier between the signal terminal and the electrode, the electrode assembly further including a cover that surrounds the moisture barrier at least in part; and
    a signal conductor configured to couple electronically the electronics module and the signal terminal when the electrode assembly is thus coupled to the support structure and the support structure is so worn.

2. The WCD system of claim 1, in which
    the electrode includes a material that includes silicone.

3. The WCD system of claim 1, in which
    the electrode includes a material that includes a conductive silicone rubber.

4. The WCD system of claim 1, in which
    the electrode includes a material that includes polydimethylsiloxane (PDMS) silicone rubber.

5. The WCD system of claim 1, in which
    the electrode has a main surface that has holes.

6. The WCD system of claim 1, in which
    the electrode assembly further includes an electrostatic shield between the signal terminal and the electrode.

7. The WCD system of claim 6, in which
    the electrostatic shield includes a metal foil covered by a tape.

8. The WCD system of claim 1, in which
    the cover surrounds the moisture barrier shield completely.

9. The WCD system of claim 1, in which
    the electrode assembly further includes a backing which, together with the cover, completely surround the moisture barrier.

10. The WCD system of claim 1, in which
    the electrode assembly further includes an electrostatic shield between the signal terminal and the electrode.

11. The WCD system of claim 10, in which
    the electrostatic shield includes a metal foil covered by a tape.

12. A Wearable Cardiac Defibrillator (WCD) system, comprising:
    a support structure configured to be worn by a patient;
    an electronics module;
    an electrode assembly configured to be coupled to the support structure so that the electrode assembly is placed against the body physically when the support structure is so worn, the electrode assembly including an electrode, a signal terminal electrically coupled to the electrode, and an electrostatic shield between the signal terminal and the electrode, the electrode assembly further including a cover that surrounds the electrostatic shield at least in part; and
    a signal conductor configured to couple electronically the electronics module and the signal terminal when the electrode assembly is thus coupled to the support structure and the support structure is so worn.

13. The WCD system of claim 12, in which
    the electrode assembly further includes a reference terminal coupled to the electrostatic shield, and
    further comprising: a reference conductor configured to couple electronically the electronics module and the reference terminal when the electrode assembly is thus coupled to the support structure and the support structure is so worn.

14. The WCD system of claim 12, in which
    the cover surrounds the electrostatic shield completely.

15. The WCD system of claim 12, in which
the electrode assembly further includes a backing which, together with the cover, completely surround the electrostatic shield.

16. A Wearable Cardiac Defibrillator (WCD) system, comprising:
a support structure configured to be worn by a patient;
an electronics module;
an electrode assembly configured to be coupled to the support structure so that the electrode assembly is placed against the body when the support structure is so worn, the electrode assembly including an electrode, the electrode including a material that includes a conductive silicone rubber, the electrode assembly further including a signal terminal electrically coupled to the electrode, and a moisture barrier between the signal terminal and the electrode; and
a signal conductor configured to couple electronically the electronics module and the signal terminal when the electrode assembly is thus coupled to the support structure and the support structure is so worn.

17. A Wearable Cardiac Defibrillator (WCD) system, comprising:
a support structure configured to be worn by a patient;
an electronics module;
an electrode assembly configured to be coupled to the support structure so that the electrode assembly is placed against the body when the support structure is so worn, the electrode assembly including an electrode, the electrode including a material that includes polydimethylsiloxane (PDMS) silicone rubber, the electrode assembly further including a signal terminal electrically coupled to the electrode, and a moisture barrier between the signal terminal and the electrode; and
a signal conductor configured to couple electronically the electronics module and the signal terminal when the electrode assembly is thus coupled to the support structure and the support structure is so worn.

18. A Wearable Cardiac Defibrillator (WCD) system, comprising:
a support structure configured to be worn by a patient;
an electronics module;
an electrode assembly configured to be coupled to the support structure so that the electrode assembly is placed against the body when the support structure is so worn, the electrode assembly including an electrode, the electrode having a main surface that has holes, the electrode assembly further including a signal terminal electrically coupled to the electrode, and a moisture barrier between the signal terminal and the electrode; and
a signal conductor configured to couple electronically the electronics module and the signal terminal when the electrode assembly is thus coupled to the support structure and the support structure is so worn.

19. A Wearable Cardiac Defibrillator (WCD) system, comprising:
a support structure configured to be worn by a patient;
an electronics module;
an electrode assembly configured to be coupled to the support structure so that the electrode assembly is placed against the body when the support structure is so worn, the electrode assembly including an electrode, a signal terminal electrically coupled to the electrode, and a moisture barrier between the signal terminal and the electrode, the electrode assembly further including an electrostatic shield between the signal terminal and the electrode, the electrostatic shield including a metal foil covered by a tape; and
a signal conductor configured to couple electronically the electronics module and the signal terminal when the electrode assembly is thus coupled to the support structure and the support structure is so worn.

20. A Wearable Cardiac Defibrillator (WCD) system, comprising:
a support structure configured to be worn by a patient;
an electronics module;
an electrode assembly configured to be coupled to the support structure so that the electrode assembly is placed against the body physically when the support structure is so worn, the electrode assembly including an electrode, a signal terminal electrically coupled to the electrode, an electrostatic shield between the signal terminal and the electrode, and a reference terminal coupled to the electrostatic shield;
a signal conductor configured to couple electronically the electronics module and the signal terminal when the electrode assembly is thus coupled to the support structure and the support structure is so worn; and
a reference conductor configured to couple electronically the electronics module and the reference terminal when the electrode assembly is thus coupled to the support structure and the support structure is so worn.

* * * * *